United States Patent [19]

Hermann et al.

[11] Patent Number: 5,521,098
[45] Date of Patent: May 28, 1996

[54] THERMIONIC IONIZATION DETECTOR WITH FLOW-THROUGH THERMIONIC SOURCE

[75] Inventors: Bruce W. Hermann, Kennett Square; Richard P. White, West Chester, both of Pa.

[73] Assignee: Hewlett-Packard Company, Palo Alto, Calif.

[21] Appl. No.: 280,920

[22] Filed: Jul. 27, 1994

[51] Int. Cl.$^6$ .................................................. G01N 27/00
[52] U.S. Cl. ............................ 436/149; 422/54; 422/70; 422/98; 436/151
[58] Field of Search ........................... 73/23, 26; 422/98, 422/54, 70; 436/149, 153, 151, 154, 161

[56] References Cited

U.S. PATENT DOCUMENTS

| | | |
|---|---|---|
| 3,677,709 | 7/1972 | Riedmann et al. . |
| 3,959,764 | 5/1976 | Allman . |
| 4,203,726 | 5/1980 | Patterson ................................ 23/232 |
| 4,508,685 | 4/1985 | Sisti et al. ................................ 422/54 |
| 4,524,047 | 6/1985 | Patterson ................................ 422/98 |
| 4,720,421 | 1/1988 | Khilnani . |
| 4,839,143 | 6/1989 | Vora et al. ................................ 422/98 |
| 4,842,825 | 6/1989 | Martin et al. ............................. 422/80 |
| 4,958,529 | 9/1990 | Vestal .................................... 73/864.81 |
| 5,228,514 | 7/1993 | Worden et al. .......................... 165/155 |

OTHER PUBLICATIONS

"Thermionic Nitrogen–Phosphorus Detection with an Alkali–Ceramic Bead," Paul L. Patterson and Robert L. Howe, Journal of Chromatographic Science, vol. 16, Jul. 1978, pp. 275–280.
"Preparation and Characterization of Glass Beads for Use in Thermionic Gas Chromatographic Detectors," J. A. Lubkowitz, B. P. Semonian, Javier Galobardes, and L. B. Rogers, Analytical Chemistry, vol. 50, No. 4, Apr. 1978, pp. 672–676.
"The Detection Mechanism and the Response Character of the Thermionic Detector using an Alkali Salt," J. Sevcik, Chromatographia, vol. 6, No. 3, Mar. 1973, pp. 139–148.

Primary Examiner—Lyle A. Alexander
Attorney, Agent, or Firm—Mark Z. Dudley

[57] ABSTRACT

Method and apparatus for the thermionic ionization detection of one or more particular constituent components of a sample that is present in a fluid mixture. The fluid mixture flows across the interior surface of a central bore in a heated and appropriately sensitized "flow-through" thermionic source. The constituent components are ionized by an ionization process in which electrical charge is transferred from the thermionic source and converted into gas phase ion species. The current of gaseous ions is collected and measured at a collector electrode adjacent to the thermionic source.

11 Claims, 6 Drawing Sheets

THERMIONIC IONIZATION DETECTOR WITH FLOW-THROUGH THERMIONIC SOURCE

FIELD OF THE INVENTION

The present invention relates generally to thermionic ionization detectors, and in particular to a thermionic ionization detector having an improved thermionic source.

BACKGROUND OF THE INVENTION

Thermionic ionization detectors are used in the field of chromatography for the detection of specific constituent components of a sample that is present in a fluid stream. Such detectors usually include a thermionic source having a surface impregnated with an alkali metal compound so as to make the detector specifically sensitive to a halogen, nitrogen, or phosphorus compound. An electrical heating current, carried by a resistive heating wire embedded in the thermionic source, heats the thermionic source. Certain sample compounds, or their decomposition products, extract the electrical charge from the hot thermionic surface of the source. Ions form on the surface of the thermionic source and migrate through a fluid stream flowing past the thermionic source to a collector electrode. The resulting ion current is collected at the collector electrode. An electronic current-measuring circuit, such as an electrometer, measures the ion current arriving at the collector electrode.

The ionization mechanism in these thermionic detectors is believed by some practitioners to be a surface ionization process rather than a gas phase process. (See, for example, Patterson, *Journal of Chromatography*, Vol. 167, p. 381, 1978.) Prior art thermionic detection techniques have therefore attempted to improve the construction and performance of the thermionic source. For example, U.S. Pat. No. 2,795,716 discloses a detector featuring a source in the form of a cylindrical alumina ceramic core upon which is wound a heater coil; U.S. Pat. No. 3,852,037 discloses the deposition of a material in the form of a bead onto an electrical heating wire to form a thermionic source.

Accordingly, FIGS. 1-A through 1-D represent the typical shapes and configurations of the ion collector (C), thermionic source (S), and sample inlet (I) in commercially available detectors. In FIGS. 1-A and 1-C, the source (S) is formed as an alkali-glass bead fused on a heating wire in the shape of a loop. In FIG. 1-B, the source (S) includes a heater wire wrapped on a ceramic core having an alkali-glass material fused over the outer surface to form a bead. In FIG. 1-D, the source (S) includes a sub-layer coating of ceramic cement and a non-corrosive, metallic compound additive, and a surface layer of a mixture of ceramic cement and an alkali metal compound additive, that are molded about a loop of heating wire to form a solid cylindrical bead. A conventional thermionic source is thus designed as a solid element that is positioned within the fluid stream. When the fluid stream is flowing, the majority of the contact of the fluid stream with the thermionic source occurs on the leading (upstream) portion of the exterior of the thermionic source.

The sensitivity of conventional thermionic ionization detectors is affected by changes in the interaction of the fluid stream with the thermionic source (S). For example, variations in the fluid stream flow rate, or erosion of the surface of the thermionic source, can alter the contact area of the fluid stream on the thermionic source (S). As a result, there is a variation in the amount of fluid that interacts with the alkali-metal compounds in the thermionic source and the accuracy and the sensitivity of the detector is not suitable for some applications.

Moreover, the alkali-metal compounds in the thermionic source are corrosive to the metallic heating wire that is typically employed to heat the alkali compounds; some samples include chemical components that are corrosive as well. Corrosion of the heating wire is known to cause detector failure and accordingly conventional approaches have attempted to decrease the exposure of the wire to corrosion. One such approach includes coating the metallic heating wire with a sub-layer comprised of non-corrosive ceramic material or a mixture of ceramic material and an inorganic, electrically conductive and non-corrosive chemical additive. See, for example, U.S. Pat. No. 4,524,047. However, the success of this approach depends upon the integrity of the coating; the development of voids or cracks in the coating during manufacture or operation can lead to corrosion.

SUMMARY OF THE INVENTION

This invention provides a method and apparatus for an improved thermionic ionization detection of one or more particular constituent components of a sample that is present in a fluid mixture. The fluid mixture is restricted to passage across the interior surface of a bore in a flow-though thermionic source. The constituent components are ionized by electrical charge transferred from the thermionic source and are converted into gas phase ion species. A current of gaseous ions is collected and measured at a collector electrode adjacent to the thermionic source.

In a preferred embodiment of the present invention, a thermionic ionization detector may be constructed to include a fluid mixing structure for providing a fluid mixture flow that includes a first fluid. A flow-through thermionic source is formed of a matrix including an alkali metal compound which is capable of ionization of the constituent component to produce an ion current when operated at an elevated temperature. The matrix includes an interior surface that defines a central bore. A collector electrode for receiving the ion current is provided. A fluid-directing structure is provided to align the flow-through thermionic source and the collector body in a spaced relationship and direct the fluid mixture flow through the central bore of the thermionic source to the collector electrode. An ion current measuring device is provided for determining the ion current received by the collector electrode.

Preferably, the central bore is cylindrical and thus maintains a nearly constant surface area while eroding.

DETAILED DESCRIPTION OF THE PREFERRED EMBODIMENTS

The present invention will find useful application in a variety of fluid analysis systems that benefit from the detection of one or more particular constituent components of a sample present in a fluid mixture. Such systems are commonly employed in a wide variety of applications, such as sample analysis or purification, chemical analysis, clinical assay, environmental monitoring or sensing, industrial processing, and water purification. Further examples that are particularly benefited by use of the present invention include supercritical fluid chromatography and high pressure gas chromatography.

Figure 1A:
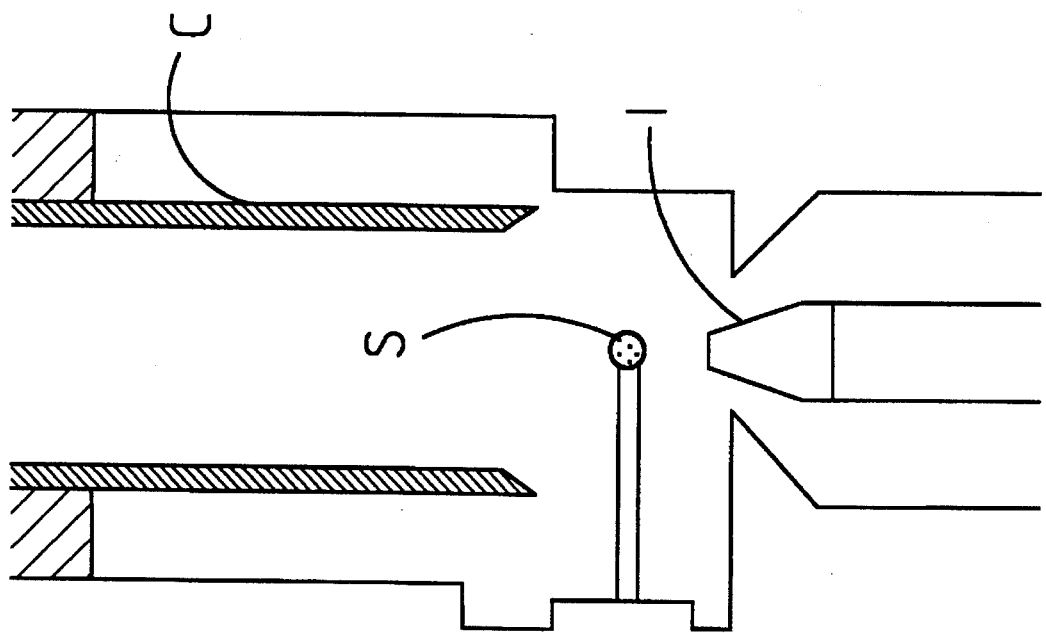
FIGS. 1A–1D are simplified schematic illustrations that represent the construction of thermionic sources employed in thermionic ionization detectors found in the prior ad.
Figure 1B:
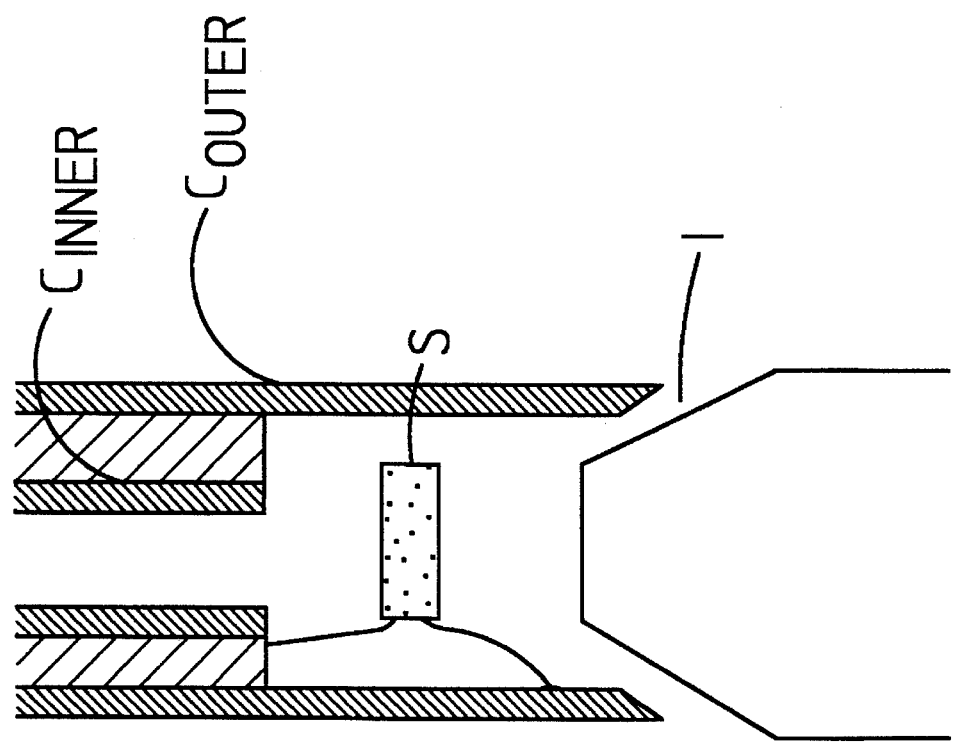
Figure 1C:
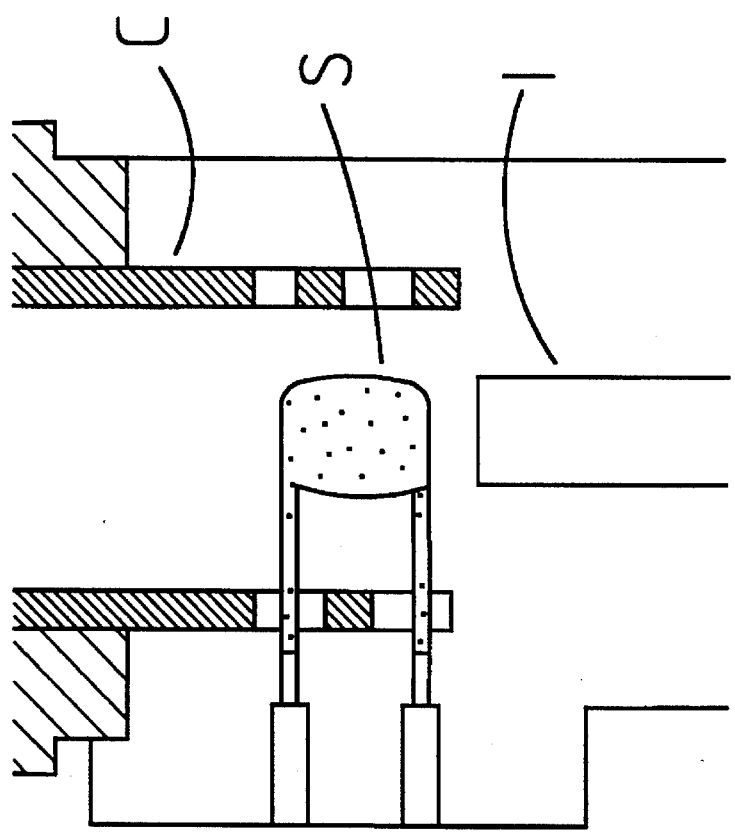
Figure 1D:
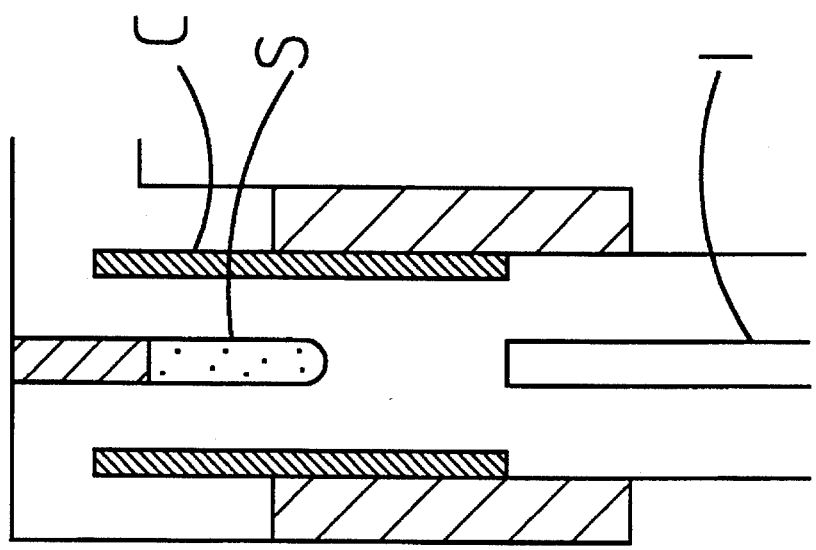
Figure 2:
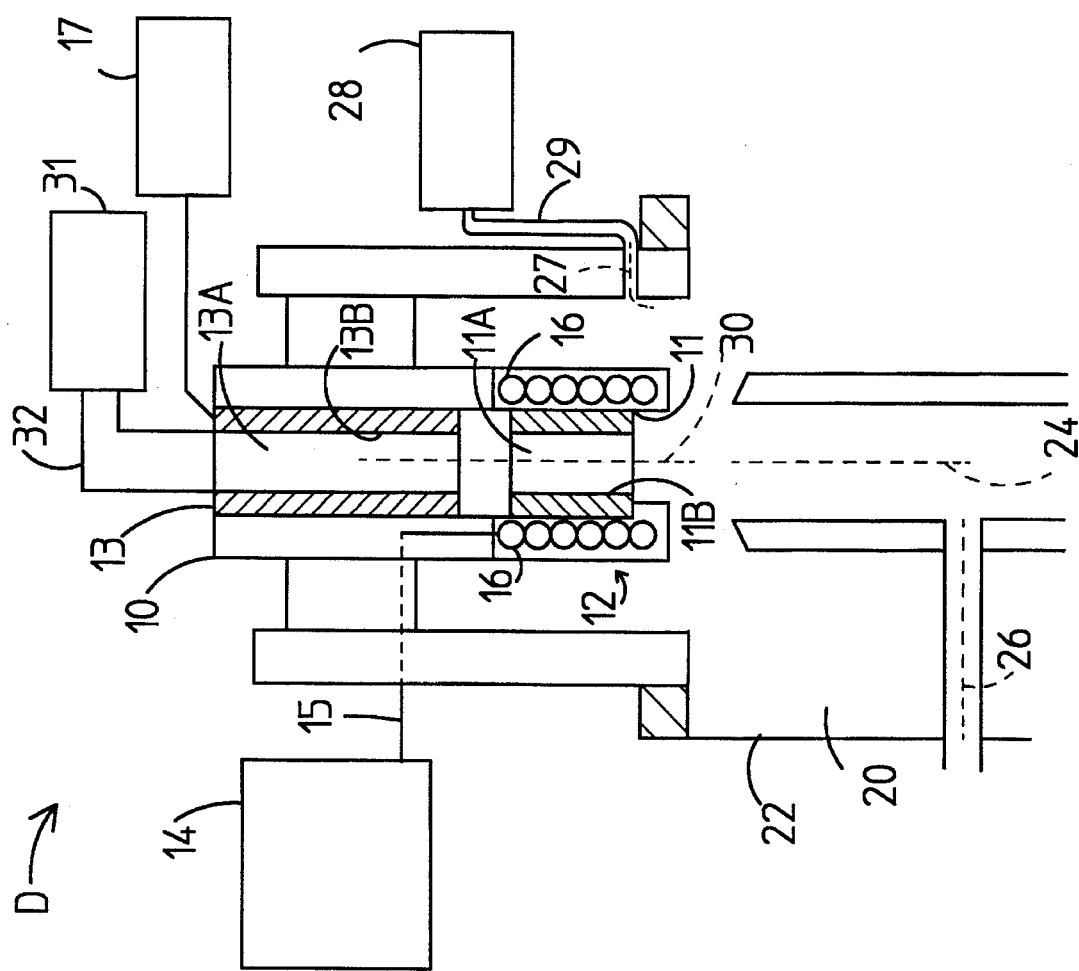
FIG. 2 is a simplified schematic illustration of a thermionic ionization detector constructed according to the present invention.

FIG. 2 shows a schematic illustration of the electronic and mechanical components of a first preferred embodiment of a thermionic ionization detector (D) constructed to include a flow-though thermionic source (hereinafter, simply termed as the thermionic source (11)), a radiant heater assembly (12), and a collector electrode (13) according to the present invention. The cylindrically-shaped thermionic source (11) and the collector electrode (13) are coaxially aligned and closely fitted to the interior of a passageway defined by a fluid-directing structure (10). An electronic power supply (14) provides a selectably controlled amount of electrical current or voltage on electrical leads (15) to cause a controlled emission of radiant energy from a radiant heating element (16) that is directed to the thermionic source (11). The radiant energy, absorbed by the thermionic source (11), causes the thermionic source to achieve a predetermined elevated temperature. In response, alkali metal atoms in the interior surface (11B) of the thermionic source (11) effect a surface of low work function which is capable of transferring electrical charge while operated at the elevated temperature. The collector electrode (13) is electrically connected to an ion current measurement device (17) such as an electrometer which is used to measure the magnitude of ionization current that flows from the thermionic source to the collector electrode (13).

A fluid mixing structure (22) includes a chamber (20) for directing a first fluid (24), a first detector fluid (26), and a second detector fluid (27) toward the thermionic source (11). Preferably, the first fluid comprises a heated, gaseous combination (under pressure) of the sample that is to be analyzed and a carrier gas; the first detector fluid comprises pressurized hydrogen and (optionally) a make-up gas; and the second detector fluid comprises air at ambient pressure and temperature. The second detector fluid (27) is provided via a conduit (29) between the fluid mixing structure (22) and a second detector fluid source (28).

The aforementioned fluids (24, 26, 27) combine to form a fluid mixture (30) that is restricted to pass through a central bore (11A) defined by the smooth interior surface (11B) of the thermionic source (11) prior to passing through a second central bore (13A) defined by the smooth interior surface (13B) of the collector electrode (13). The thermionic source (11) is termed "flow-through" to denote the use of the central bore (11A) for substantially all fluid contact of the fluid mixture (30) with the thermionic source (11). In the preferred embodiment, the central bore (11A) is cylindrical, such that any erosion of the interior surface (11 B) will have a nearly neglible effect on the surface area of the interior surface (11B). Accordingly, the contact of the fluid mixture (30) with the thermionic source (11) is more complete, uniform, and consistent, and less subject to variations in the direction or flow rate of the fluid mixture, than is experienced by thermionic sources in the prior art. A vent tube (32) allows the further passage of the fluid mixture (30) from the second central bore (13A) to an analytical instrument (31), such as a mass spectrometer, that may be optionally included for further analysis of the fluid mixture as known in the art.

Figure 3:
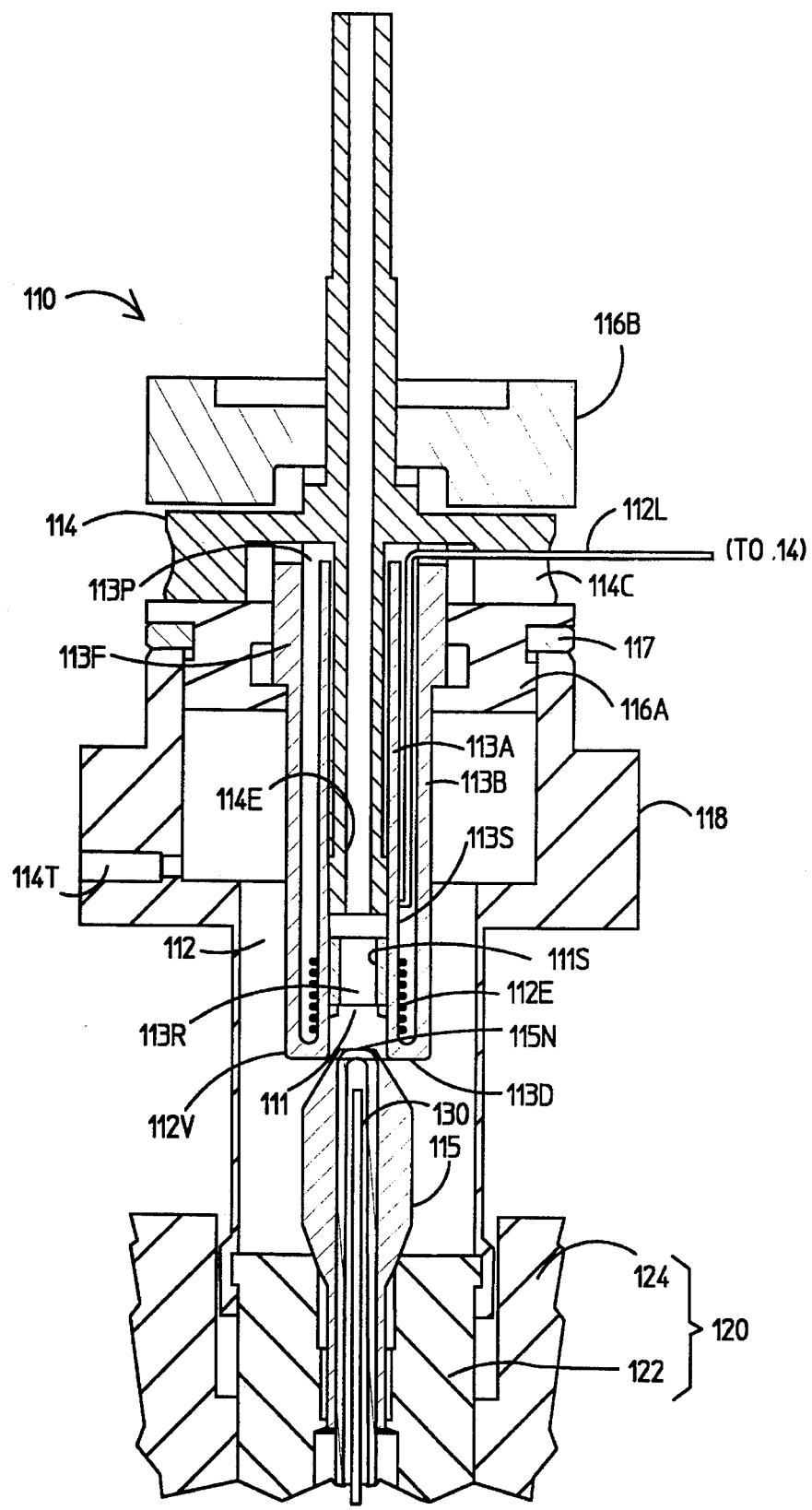
FIG. 3 is a cross-sectional illustration of the thermionic ionization detector of FIG. 2.

FIG. 3 shows a cross-sectional view of a second preferred embodiment of a thermionic ionization detector (110) constructed according to the present invention. A cylindrical flow-through thermionic source (111) is composed of a glassy amorphous matrix, preferably fused silica, that includes a predetermined concentration of an alkali metal compound additive. Alkali metal atoms in the surface layer of the interior surface (111S) produce a surface of low work function when operated at an elevated temperature preferably in the range of approximately 100 degrees C. to 1000 degrees C. A radiant heater assembly (112) includes a radiant heating element (112E) suspended in an envelope (112V). The radiant heating element (112E) responds to an applied electrical current from the electronic power supply (14) (see FIG. 2) by emitting radiant energy, preferably in the infrared region, which heats the thermionic source (111) to a selected elevated temperature. Preferably, the elevated temperature is selected from temperatures in the range of from about 500 degree(s) C. to about 1000 degree(s) C.

The envelope (112V) is formed as a tubular, concentric double-wall structure composed of an inert material. The envelope (112V) includes inner and outer walls (113A, 113B) that are formed from a single-drawn, fluid-tight structure of fused quartz or fused silica, which is transmissive of infrared radiant energy. ("Fused quartz" and "fused silica" are generally equivalent terms that are used herein to refer to an inert, amorphous glassy composition that may include one of many forms of vitreous silica and the material formed by direct melting of quartz crystals.) The walls (113A, 13B) are fused together at the bottom of the assembly so as to form a rounded aperture (113D) that defines a central bore (113R). The walls (113A, 113B) are concentric so as to offer at least three functions: firstly, to support the heating element (112E) in a manner so as to isolate the element from the corrosive effects of the alkali metal or the sample in the fluid mixture; secondly, to maximize the absorption of radiant energy by the thermionic source (110), and to minimize the loss of radiant energy; and thirdly, to provide an opening (113P) by way of a flange (113F) to allow installation or removal of the heating element (112E). The outer wall (113B) is preferably treated or altered so as reflect the radiant energy inward to the thermionic source (111) by, for example, application of an energy-reflective coating, such as a layer of platinum, silver, or nickel. Low resistance heater element leads (113L) attach to the heating element (112E) and exit through a collector body (114) by way of a side channel (114C).

The first fluid stream (comprising a mixture of sample, carrier fluid, and make-up fluid) is directed by a jet (115) from a nozzle (115N) positioned coaxially with the thermionic source (111) and the envelope (112V) such that the first fluid stream will combine with a second fluid stream supplied by a supply tube (114T). The combination of the first and second fluid streams (hereinafter, the fluid stream mixture) enters the aperture (113P) and then (due to the close fit of the thermionic source (111) to the inner wall (113A)) is restricted to impinge upon the interior surface (111S) of the thermionic source (111) before reaching the collector electrode section (114E) of the collector body (114). In operation, the interior surface (111S) of the thermionic source (111) is thereby exposed to substantially all of the sample conveyed by the fluid stream mixture. Sample compounds that are electronegative in chemical structure, and therefore readily form gas phase negative ions by the attachment of electrons or negative ions, are ionized by extracting negative charge from the interior surface (111S) of the source. The collector electrode (114E), which is electrically connected by way of the collector body (114) to the electrometer (17 shown in FIG. 2), receives an ionization current at the collector electrode (114E).

The radiant heater assembly (112) and collector body (114) are concentrically clamped onto a detector base (118) by first and second electrically insulating sleeves (116A, 16B) that are preferably formed of materials, such as inert polymers, that are creep-resistant and inert to the fluid stream mixture and the elevated temperatures caused by the heater assembly (112). Exemplary inert polymers are polyimides, aramid polymers, and poly(tetrafluoroethylene) such as are available from the DuPont Company (Wilmington, Del.) under the tradenames Vespel, Kevlar, and Teflon, respectively; and poly(chlorotrifluoroethylene), such as available from the 3M Company (Newark, N.J.) under the tradename Kel-F. A gasket (117), preferably formed of a temperature-resistant resilient material such as silicone, provides a fluid-tight joint between the first insulating sleeve (116A) and the detector base (118). The detector base (118) is attached to a supporting assembly (120) that includes a base sleeve (122) and heated block (124). A capillary column (130) inserted into the jet (115) so as to terminate at a point proximate the nozzle (115N) is preferred for transporting the first fluid stream from a sample inlet (not shown). The capillary column (130) is preferably formed of fused silica.

The radiant heating element (112E) includes a resistive filament of approximately 0.2 to 0.4 mm platinum (Pt), nichrome (Ni-Cr), or iron-chromium-aluminum (Fe-Cr-Al) alloy formed as a helical coil of a diameter of approximately 6 to 10 mm so as to be positionable between the inner and outer walls (113A, 113B). A preferred wire composition is iron-chromium-aluminum (Fe-Cr-Al) alloy, available as KANTHAL A-1 resistance heating alloy, manufactured by the Kanthal Corporation (Bethel, Conn.). The leads (112L) each are preferably formed from an approximately 20 mil nickel wire having a ceramic insulating sleeve. These dimensions are not to be considered restrictive, and larger or smaller dimensions can be used with corresponding adjustments in, for example, the structure of the radiant heater assembly (112) and the magnitude of electrical current supplied to the radiant heating element (112E).

The thermionic source (111) is preferably formed of one or more alkali-metal compounds set in a matrix or substrate. In the preferred embodiment, the thermionic source (111) is composed of a removeable, drawn-glass hollow cylindrical matrix of fused silica or fused quartz that has been enriched with one or more alkali-metal compounds. An example of a suitable fused silica or fused quartz material includes Heraeus powdered quartz, manufactured by Heraeus Amersil Company (Buford, Ga). An alternative composition would include a hollow cylinder of hardened ceramic material formed from a slurry that includes a mixture of proportionate amounts of water, ceramic cement, and an alkali-metal compound. The ceramic cement preferably contains inorganic constituents such as $Al_2O_3$ or $SiO_2$. An example of a suitable ceramic cement is Ceramacast Type 505 Cement, manufactured by AREMCO Products, Inc. (Ossining, N.Y.)

Generally, the amount and type of alkali-metal compound are selected according to the intended type of surface ionization process sought. Alkali metal compound additives in proportionate amounts ranging from a trace amount by weight to 40% by weight (with respect to the above-described glassy or ceramic matrix) will exhibit useful ionization characteristics under various operating conditions of the thermionic source (111). These additives may include compounds of any of the class of alkali metals that includes Cs, Rb, K, Na, and La, and in some instances may include a combination of more than one type of alkali metal compound. Specific requirements for the alkali metal compounds used are that they must have a low volatility at the selected temperature of the thermionic source. Alkali sulfate compounds, alkali carbonates, and alkali chlorides have been found to be suitable. For example, compositions that include $Cs_2SO_4$ and ceramic cement will provide specific ionization of sample compounds containing nitrogen or phosphorus atoms. In the glassy matrix, a preferred additive is a Rubidium salt, such as 99.9% Rubidium carbonate ($Rb_2CO_3$) or Rubidium Sulfate ($Rb_2SO_4$) manufactured by Alfa/Johnson Matthey, Ward Hill, Mass.

Any potentially corrosive effects of the fluid flow mixture (30) or the alkali metal in the thermionic source (111) on the heating element (112E) and leads (112L) are thus precluded by the fluid-tight enclosure of the element (112E) and leads (112L) within the envelope (112V), flange (112F), and side channel (114C) in the collector (114).

In the preferred application of the above-described embodiments of a thermionic ionization detector, the first fluid flow is taken from the effluent gas stream of a gas chromatograph instrument. However, the preferred embodiment of the present invention is not limited in application to use as a thermionic ionization detector for a gas chromatograph instrument. Because the contemplated thermionic source (111) provides selective ionization of certain types of chemical substances, this source can also be used in the detection of the presence of these specific chemical substances in any fluid environment. It is also recognized that the preferred embodiment of the present invention can be modified for use as a means of converting molecules of certain types of chemical substances into gas phase negative ions for the purpose of subsequent analysis of charge-to-mass ratio by a mass spectrometer instrument, or mass and size analysis by an ion mobility apparatus. For such applications, the collector (114) would be plumbed to allow the passage of gas phase ions into the subsequent analysis equipment. The possibility of effecting further ion analysis is illustrated diagrammatically in FIG. 2 by the analytical instrument (31).

It is to be recognized that variations in the composition or general shape of the contemplated thermionic source and modifications in the dimensions or configuration of the thermionic detector might be appropriate for certain applications and yet be within the scope of this invention. For example, further embodiments of a flow-through thermionic source may be provided in an annular, elliptical, or toroidal shape, if a central bore is provided to achieve the above-described "flow-through" characteristic.

Although the invention has been described with reference to the above-described preferred embodiments, variations and modifications are contemplated as being within the scope and spirit of the present invention.

What is claimed is:

1. A thermionic ionization detector for detecting the presence of a constituent component of a sample in a first fluid, comprising:

a fluid mixing structure for providing a fluid mixture flow that includes the first fluid;

a flow-through thermionic source having a matrix including an alkali metal compound that is capable of ionization of the constituent component to produce an ion current when operated at an elevated temperature, the matrix having an interior surface that defines a central bore;

a collector electrode for receiving the ion current;

a fluid-directing structure for aligning the flow-through thermionic source and the collector electrode in a spaced relationship and for confining substantially all of the fluid mixture flow through the central bore of the thermionic source to the collector electrode; and an ion current measurement device for determining the ion current received by the collector electrode.

2. The apparatus of claim 1, wherein the matrix includes an amorphous glassy composition selected from the group consisting of silica and quartz.

3. The apparatus of claim 1, wherein the matrix includes a ceramic composition.

4. The apparatus of claim 1, wherein the alkali metal compound includes at least one alkali metal selected from of the group consisting of Cs, Rb, K, Na, and La.

5. The apparatus of claim 1, wherein the interior surface of the thermionic source is of generally cylindrical configuration.

6. The apparatus of claim 1, wherein said collector electrode comprises a second central bore of generally cylindrical configuration for passage of the fluid mixture therethrough.

7. The apparatus of claim 6, wherein the central bore of the thermionic source and the second central bore of the collector electrode are coaxially aligned in the fluid-directing structure.

8. The apparatus of claim 1, wherein the fluid mixing structure further comprises means for mixing first and second detector fluids with the first fluid.

9. The thermionic ionization detector of claim 8, wherein the first detector fluid comprises hydrogen and the second detector fluid comprises air, and further comprising first and second detector fluid sources.

10. A thermionic ionization detector for detecting the presence of a constituent component of a sample in a first fluid, comprising:

a fluid mixing structure for providing a fluid mixture flow that includes the first fluid, a first detector fluid, and a second detector fluid;

a flow-through thermionic source having a matrix including an alkali metal compound that is capable of ionization of the constituent component to produce an ion current when operated at an elevated temperature, wherein the matrix includes an amorphous glassy composition formed to include an interior surface that defines a central bore;

a collector electrode for receiving the ion current;

a fluid-directing structure for coaxially aligning the central bore of the thermionic source and the collector body in a spaced relationship and for confining substantially all of the fluid mixture flow through the central bore of the thermionic source to the collector electrode; and an ion current measuring device for determining the ion current received by the collector electrode.

11. A method for detecting the presence of a constituent component of a sample in a first fluid, comprising the steps of:

providing a flow-through thermionic source having a matrix including an alkali metal compound which is capable of ionization of the constituent component to produce an ion current when operated at an elevated temperature, the matrix having an interior surface that defines a central bore;

providing a collector electrode for receiving the ion current;

aligning the flow-through thermionic source and the collector electrode in a spaced relationship;

providing a fluid mixture flow that includes the first fluid;

confining substantially all of the fluid mixture flow through the central bore of the thermionic source to the collector electrode; and determining the ion current received by the collector electrode and, in response, indicating the presence of the constituent component.

* * * * *